(12) United States Patent
Velasco Valcke

(10) Patent No.: US 11,660,461 B2
(45) Date of Patent: May 30, 2023

(54) TISSUE-STIMULATION DEVICE WITH OUTPUT DEMULTIPLEXER

(71) Applicant: PANACEA QUANTUM LEAP TECHNOLOGY LLC, Dallas, TX (US)

(72) Inventor: Francisco Javier Velasco Valcke, Bogotá (CO)

(73) Assignee: PANACEA QUANTUM LEAP TECHNOLOGY LLC, Dallas, TX (US)

( * ) Notice: Subject to any disclaimer, the term of this patent is extended or adjusted under 35 U.S.C. 154(b) by 28 days.

(21) Appl. No.: 16/954,664

(22) PCT Filed: Dec. 20, 2018

(86) PCT No.: PCT/IB2018/060476
§ 371 (c)(1),
(2) Date: Jun. 17, 2020

(87) PCT Pub. No.: WO2019/123395
PCT Pub. Date: Jun. 27, 2019

(65) Prior Publication Data
US 2020/0312454 A1 Oct. 1, 2020

(30) Foreign Application Priority Data
Dec. 20, 2017 (CO) .................. NC2017/0013221

(51) Int. Cl.
*A61N 2/02* (2006.01)
*A61N 1/40* (2006.01)
(Continued)

(52) U.S. Cl.
CPC ............... *A61N 2/02* (2013.01); *A61F 7/007* (2013.01); *A61H 23/00* (2013.01); *A61N 1/40* (2013.01);
(Continued)

(58) Field of Classification Search
CPC ............. A61F 2007/0075; A61N 2/00; A61N 2/002; A61N 2/004; A61N 2/006; A61N 2/008;
(Continued)

(56) References Cited

U.S. PATENT DOCUMENTS 5,658,322 A 8/1997 Fleming
5,718,662 A 2/1998 Jalinous
(Continued)

OTHER PUBLICATIONS

International Search Report dated Apr. 18, 2019 for PCT/IB2018/060476.
Written Opinion of the International Searching Authority dated Apr. 18, 2019 for PCT/IB2018/060476.

*Primary Examiner* — Carrie R Dorna
(74) *Attorney, Agent, or Firm* — Fountainhead Law Group P.C.

(57) ABSTRACT

A tissue stimulation device comprising: a source; a control unit; a decoupled output stage circuit connected to the source and the control unit; a signal generator connected to the input of the decoupled output stage circuit and the control unit; an analog demultiplexer connected to the output stage circuit decoupled by a PE signal and an out signal, the analog demultiplexer is connected to the control unit, and a transducer array is connected to the output of the analog demultiplexer; wherein the control unit selects the output of the analog demultiplexer that allows switching of the PE and out signals to activate the transducers in the transducer array to stimulate tissue.

20 Claims, 6 Drawing Sheets

(51) Int. Cl.
*A61N 2/00* (2006.01)
*G16H 20/40* (2018.01)
*G16H 20/30* (2018.01)
*A61F 7/00* (2006.01)
*A61H 23/00* (2006.01)
*G06F 13/42* (2006.01)
*G16H 40/67* (2018.01)

(52) U.S. Cl.
CPC .............. *A61N 2/002* (2013.01); *G06F 13/42* (2013.01); *G16H 20/30* (2018.01); *G16H 20/40* (2018.01); *A61F 2007/0075* (2013.01); *G06F 2213/40* (2013.01); *G16H 40/67* (2018.01)

(58) Field of Classification Search
CPC .... A61N 2/02; A61N 1/36014; A61N 1/3603; A61N 1/36034; A61N 1/40
See application file for complete search history.

(56) References Cited

U.S. PATENT DOCUMENTS

| | | |
|---|---|---|
| 8,880,178 B2 * | 11/2014 | Popovic ............. A61N 1/36067 607/48 |
| 2005/0216062 A1 | 9/2005 | Herbst |
| 2011/0046687 A1 | 2/2011 | Naschberger |
| 2017/0106189 A1 * | 4/2017 | Keller ................ A61N 1/36031 |
| 2017/0157431 A1 | 6/2017 | Cheatham, III et al. |

* cited by examiner

TISSUE-STIMULATION DEVICE WITH OUTPUT DEMULTIPLEXER

CROSS REFERENCE TO RELATED APPLICATIONS

This application is the National Stage of International Application No. PCT/IB2018/060476, filed Dec. 20, 2018, and claims benefit of Columbian Patent Application No. NC2017/0013221 filed on Dec. 20, 2017, both of which are incorporated herein in their entirety.

FIELD OF THE INVENTION

This invention refers to a tissue stimulation device. The device is characterized by having an analog Demultiplexer that manages a series of transducers to stimulate tissue.

BACKGROUND OF THE INVENTION

Nowadays, current tissue stimulation devices comprise a coupled stimulation unit for at least one transducer. The transducers are adapted to deliver stimulation to tissue.

State-of-the-art discloses devices for tissue stimulation, such as those of documents U.S. Pat. Nos. 5,718,662 y 5,658,322.

On the one hand, document U.S. Pat. No. 5,718,662 discloses a stimulator for neuromuscular tissues, which has a coil that is energized at different times by a bank of discharge capacitors. The discharge capacitor bank is connected to a bank of discharge circuits, which vary the amplitude and/or the frequency of a train of stimulation pulses, for the tissue to be treated.

However, the magnetic stimulation device disclosed by document U.S. Pat. No. 5,718,662 employs individually controlled discharge capacitors, which makes the stimulation device substantially complex as the number of stimulation coils increases. The use of thyristors for their preferred modality as an element to control the discharge of the capacitor bank supposes a limitation and risks for the tissue to be stimulated because the capacitor must be completely discharged on the tissue in each discharge cycle, which could cause the tissue overstimulation.

On the other hand, document U.S. Pat. No. 5,658,322 discloses a system and a method for generating bioactive frequencies, which comprises a specific frequency generator, a control unit connected to the frequency generator, an output circuit to amplify a stimulation signal and an electrode connected to the output circuit and a subject to be stimulated. In this case, the control unit is in charge of establishing the frequency of the bioactive frequency generator and the output circuit allows said signals to be gradually amplified to be applied to the subject employing the electrodes connected to the output circuit.

Based on the above, it can be noted that the device disclosed by document U.S. Pat. No. 5,718,662 does not disclose an analog demultiplexer that in the current invention allows different activation rates to be configured for the transducers, allowing better control over the stimulation that is being performed, and try different stimulation methods.

However, the device showed in document U.S. Pat. No. 5,658,322 does not allow to dose the power of the source by varying the amplitude on demand, due to this it is not possible to apply an adequate stimulus to the tissue. The device limits the working voltage to 50V since the stimulated subject's tissue can be damaged, thus it also limits the benefits that the stimulated tissue can receive.

It is observed that, in the state of the art, no system allows distributing the power supplied to the transducers and to change their operating sequences.

BRIEF DESCRIPTION OF THE INVENTION

The present invention details a tissue stimulation device comprising: a source, a decoupled output stage circuit connected to the source, a signal generator connected to the input of the decoupled output stage circuit and a control unit, the control unit is connected to the signal generator and an analog demultiplexer via a control bus, the analog demultiplexer is connected to the control unit and the decoupled output stage circuit, and a transducer array connected to the outputs of the analog demultiplexer through a data bus.

In one embodiment of the invention, the decoupled output stage circuit and the analog demultiplexer are connected by a PE signal and an out signal.

The present invention details a tissue stimulation device comprising: a source, a control unit, a signal generator connected to the control unit, a decoupled output stage circuit connected to the source and the signal generator, an analog demultiplexer connected to the control unit and the decoupled output stage circuit, an array of transducers connected to the analog demultiplexer; wherein the control unit commands the signal generator to generate an activation signal that is applied to the transducer array through the analog demultiplexer and the decoupled output stage circuit.

In one embodiment of the present invention, the tissue stimulation device has a transducer interface between the analog demultiplexer and the transducer array. Said transducer interface has a power stage that allows supplying electrical power to each transducer.

The transducers of the transducer array are selected among others, from coils to generate a magnetic field, Helmholtz coils, electrodes to induce an electric current, Peltier cells for cold/heat stimulation, heat generators, vibration motors, inductive stimulation coils, antennas and combinations of these.

At the output of the analog demultiplexer, instead of the transducer array at the output of the analog demultiplexer which includes a power stage that allows dosing the supply of electrical power to the transducers of the transducer array.

The power stage can be performed with a variable gain operational amplifier configured in non-inverter or inverter amplifier mode, or with an amplification circuit known as a common collector transistor, which is a circuit for amplifying current, in the case of using coils as magnetic field generators (e.g. Helmholtz coils). This configuration is useful since the main source of a magnetic field with a winding is the current through the copper of the coil.

Therefore, and unlike the-state-of-the-art that discloses devices for electrical or magnetic stimulation, in tissues, the present invention allows different activation configurations of the transducers. For example, different activation sequences allowing the device to be adapted to carry out different treatments if necessary, or to add new functionalities.

DETAILED DESCRIPTION OF THE INVENTION

Figure 1:
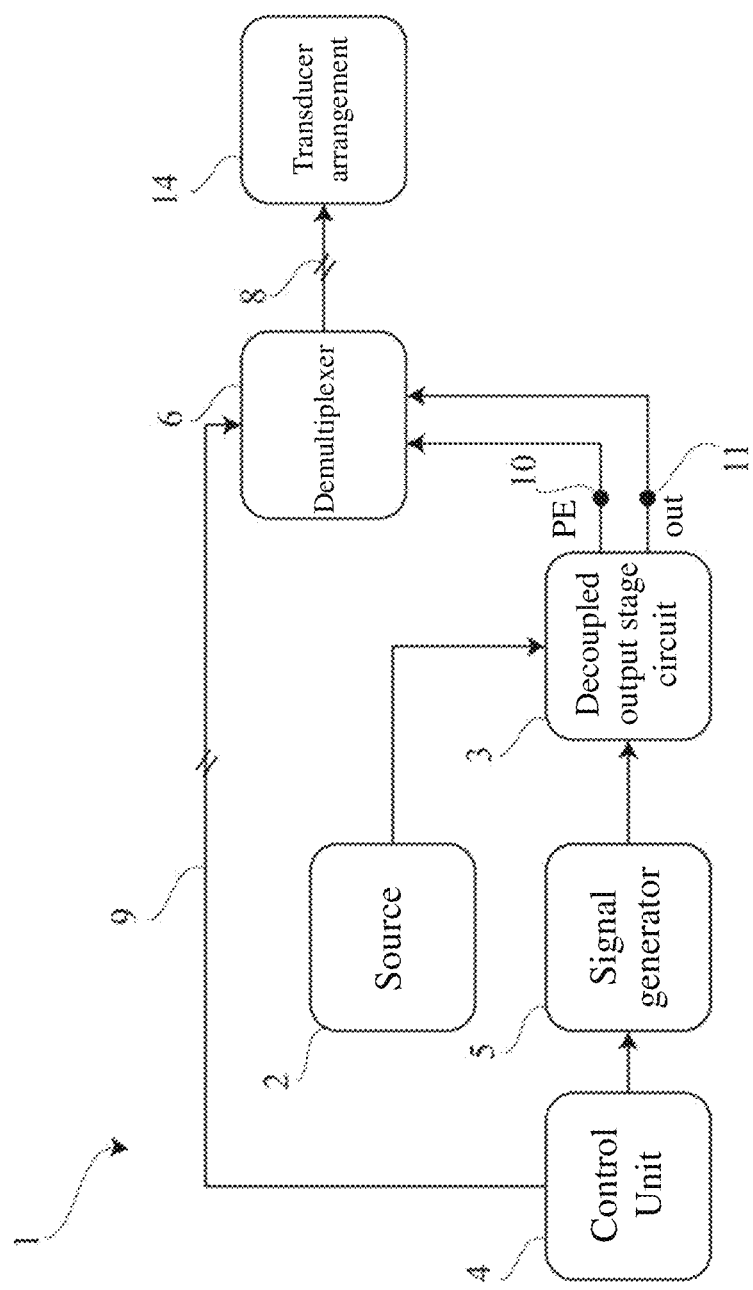
FIG. 1 shows a block diagram for the embodiment of the present invention.

FIG. 1 shows a particular embodiment of a tissue stimulation device (1) comprising: a source (2); a control unit (4); a decoupled output stage circuit (3) connected to the source (2); a signal generator (5) connected to the input of the decoupled output stage circuit (3) and the control unit (4); an analog demultiplexer (6) connected to the control unit (4) and the decoupled output stage circuit (3); and an array of transducers (14) connected to the output of the analog demultiplexer (6); the control unit (4) selects the output of the analog demultiplexer (6) that allows switching of PE (10) and out (11) signals to activate the transducers of the array of transducers (14) to stimulate tissue.

Optionally, in a different embodiment of the tissue stimulation device (1), the decoupled output stage circuit (3) is also connected to the control unit (4). This allows the control unit (4) to directly control the decoupled output stage circuit (3).

For the present invention, it should be understood that the decoupled output stage circuit (3) is a circuit that electrically isolates the ground from the tissue stimulation device (1), and produces an output with a ground independent from that of the signal (5).

The signal generator (5), of functions or waveforms which is an electronic device that generates both analog and digital periodic or non-periodic signal patterns.

Any person of ordinary skill in the art understands that the source (2) supplies the electrical power required for the tissue stimulation device (1), it is a device capable of maintaining a difference in electrical potential between two or more terminals such as an alternating current source, direct current source, batteries, photovoltaic source, thermoelectric source, among other devices capable of maintaining a difference in electrical potential between two or more terminals which are known to any person of ordinary skill in the art and combinations.

For the present invention, it is understood that a bus is a series of cables that work to transport data or electrical signals from one device to another. Accordingly, the control bus (9) carries the signals that allow the control unit (4) to activate, using a code, the analog demultiplexer (6) through which the device switches the PE (10) and out (11) signals. The data bus (8) is used by the analog demultiplexer (6) to activate the transducers (12) of the array of transducers (14).

The transducers (12) of the transducer array (14) are connected by a data bus (8) and are activated by the analog demultiplexer (6) sequentially according to an activation code that receives by a control bus (9) that connects it to the control unit (4). This sequence is aimed to perform various forms of stimulation, as well as to prevent the transducers from overheating, depending on its type.

Figure 2:
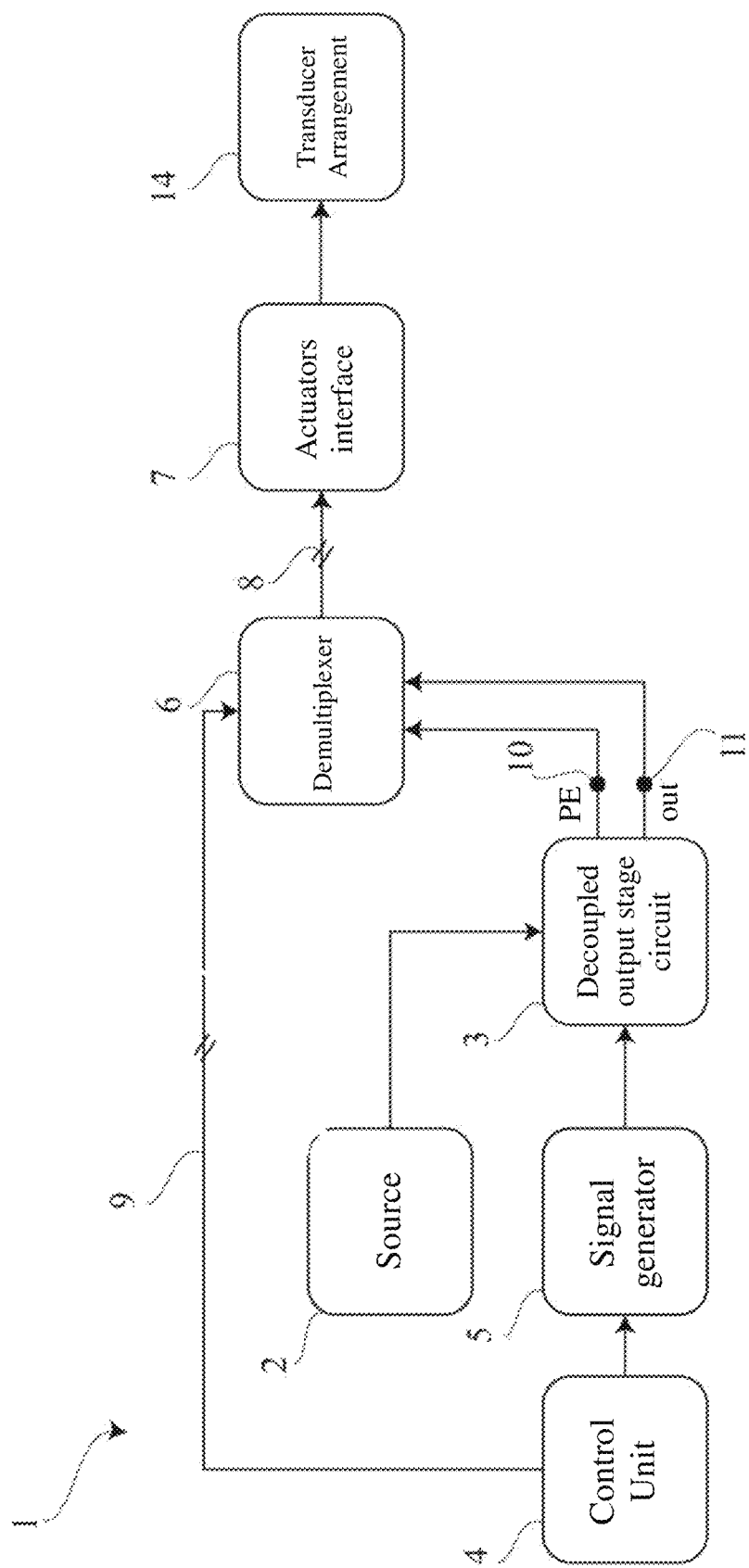
FIG. 2 shows a block diagram for the embodiment of the analog demultiplexer with a transducer interface.

In FIG. 2, a transducer interface (7) is connected to the output of the device; the interface includes a power stage that makes possible the activation of various transducers that require more power than the circuit provides through the output of the analog demultiplexer (6).

Figure 3:
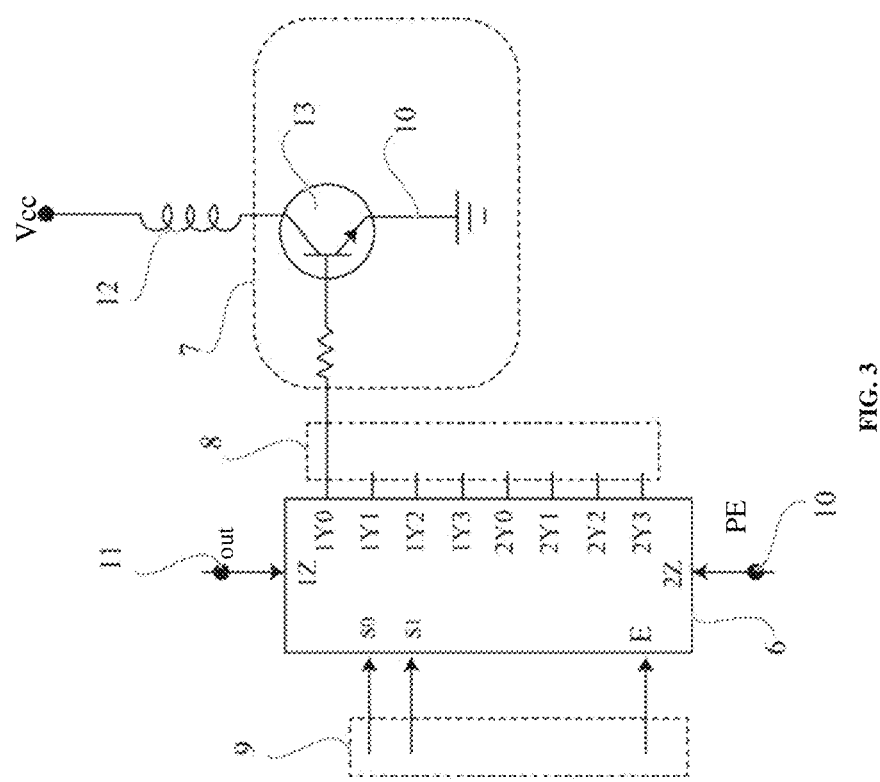
FIG. 3 shows a scheme of a different embodiment of the invention with a power stage with operational amplifiers.

The example in FIG. 3 shows that the power stage of the transducer interface (7), a transistor (13) connected with an impedance at its base to the output of the analog demultiplexer (6), a transducer is connected (12) to the transistor collector (13), and the emitter of the transistor (13) is connected to ground, the transducer (12) connected to the collector of the transistor (13) is connected to a voltage source. The control stage contains as many transistors as there are transducers in the circuit.

Figure 4:
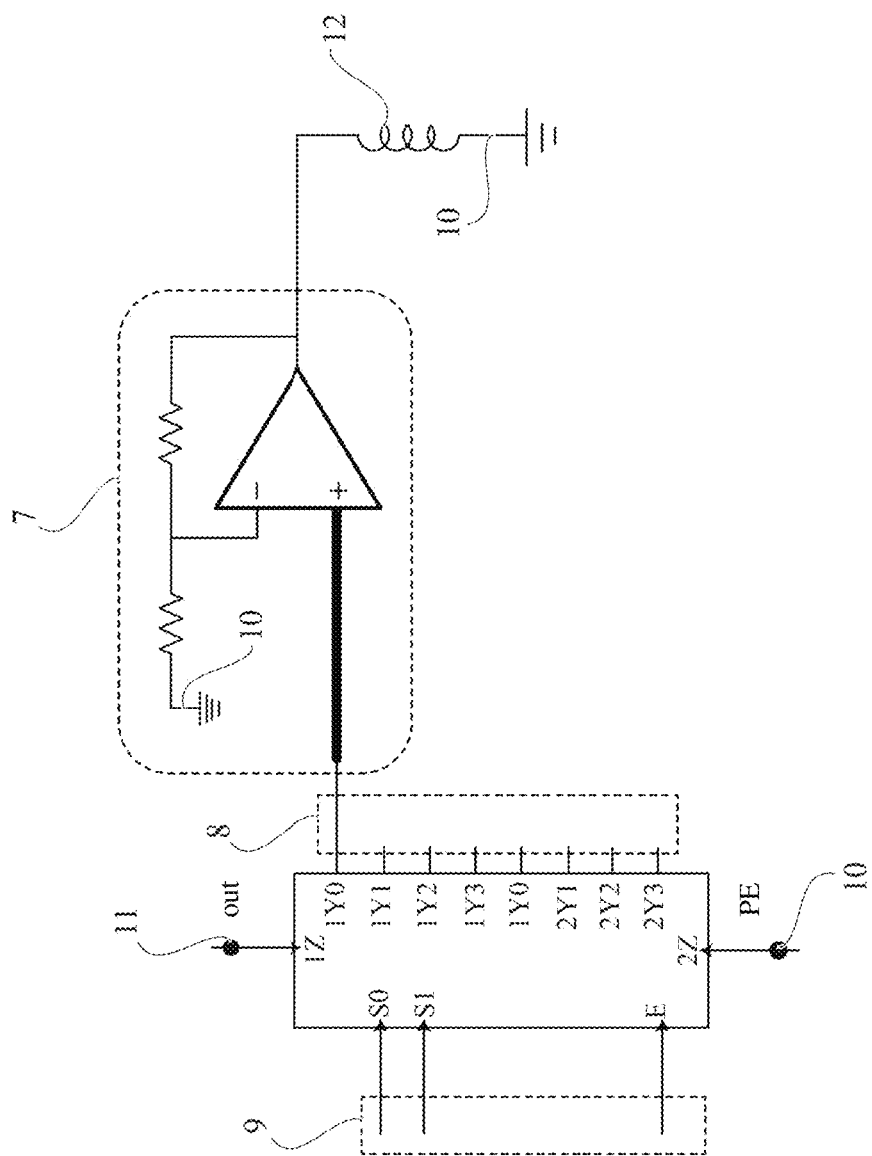
FIG. 4 shows a scheme of another embodiment of the invention with a bi-directional coil activation stage.

On the other hand, referring to FIG. 4, in a different embodiment of the present invention, for instance, a control stage consisting of an operational amplifier configured in a non-inverting mode known in the art is used. Furthermore, a power stage will include this circuit for each transducer that might need to be used in the circuit.

However, for any person of ordinary skill in the art, it is evident that any other configuration of power stage circuits is valid for the activation of the transducers or transducers that might need to be controlled in the circuit, and does not affect the ingenious concept of the present invention.

To understand the present invention, it should be assumed that a control unit is a device that processes data, for example, microcontrollers, microprocessors, DSCs (Digital Signal Controllers), FPGAs (Field Programmable Gate Arrays), CPLDs (Complex Programmable Logic Devices), ASICs (Application Specific Integrated Circuits), SoCs (System on Chips), PSoCs (Programmable System on Chips), computers, servers, tablets, cell phones, smartphones, computing units and combinations thereof known by any person with ordinary skill in the art.

The analog demultiplexer (6) is connected to the transducer interface (7) with a plurality of outputs, which in one of the types of the invention is a plurality of transducers (12), allowing coils that generate a magnetic field to be obtained and used, for example, to stimulate tissues. The transducer interface (7), in several forms of the invention, includes a power stage that amplifies each output signal from the analog demultiplexer (6) to activate the transducers (12) of the transducer array (14).

This configuration allows to configure different activation cycles, and for the control unit (4) to manage the frequencies, in case of requiring different treatment modalities.

The power stage is performed with a variable gain operational amplifier configured in non-inverter or inverter amplifier mode, or with an amplification circuit known as a common collector transistor, which is a circuit for amplifying current, in the case of using coils as magnetic field generators (e.g. Helmholtz coils). This configuration is useful since the main source of a magnetic field with a winding is the current through the copper of the coil.

Primarily, analog/digital signals must be generated using the signal generator (5) and the control unit (4) to generate the magnetic field. It is possible to select different types of signals, vary their frequency, useful duty cycle, phase, and amplitude as necessary through the control unit (4).

Once the type of signal required is generated, the signal from the control stage and the power stage is isolated to protect the electronic elements of the control stage from current and voltage changes that can be generated from the power stage. Hence, a decoupled output stage circuit (3) can be used, for example, a commercial isolation amplifier. The outputs of the decoupled output stage circuit, PE (10) and Out (11) enter an analog demultiplexer (6) that operates for analog signals.

The analog demultiplexer (6) is controlled by the control unit (4), this control unit (4) selects the outputs of the analog demultiplexer (6) connected to the transducer interface (7).

This interface has a power output that amplifies the current at the output of the analog demultiplexer (6) to activate a plurality of transducers (12) of the array of transducers (14).

The transducers (12) of the transducer array (14) are selected among others, from coils to generate a magnetic field, Helmholtz coils, electrodes to induce an electric current, Peltier cells for cold/heat stimulation, heat generators, vibration motors, inductive stimulation coils, antennas and combinations of these.

In a specific embodiment of the tissue stimulation device (1), the transducer interface (7) consists of a power stage array connected to the transducers (12) of the transducer array (14), these stages are selected from the group conformed by an array of transistors, an array of operational amplifiers, or connected directly to the output of the analog demultiplexer (6), with no amplification stage.

In FIG. 3, in one embodiment of the invention, the transducer interface (7) comprises a transistor (13) with its collector connected to a transducer (12) connected to the Vcc source, the transistor connects its emitter to a PE signal (10) by the circuit output stage decoupled (3) through the data bus (8).

Optionally, in one of the embodiment of the invention, similar to the one shown in FIG. 3, instead of a transducer (12), a coil of a relay is connected in the collector of the transistor (13), to control charging that demands a greater electric current than that supported by the transistor (13).

Figure 5:
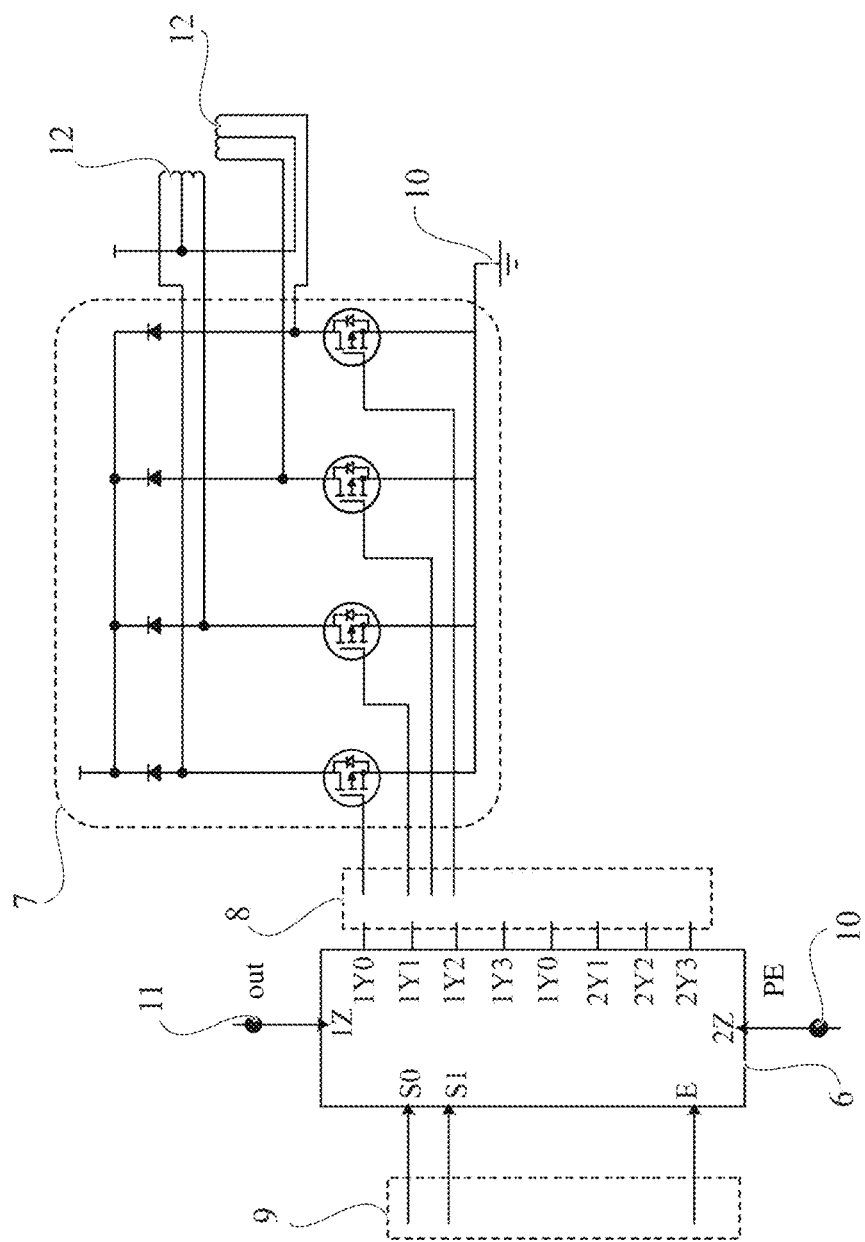
FIG. 5 shows a road map of an example of the present invention with a relay circuit.

In FIG. 5, in a different embodiment of the same invention, the power stage uses a MOSFET (Metal-oxide-semiconductor Field-effect transistor) arrangement of transistors that is connected by the gate to the output of the analog demultiplexer (6). The source of each MOSFET transistor is connected to the PE signal (10), and the drain of each MOSFET transistor is connected to the anode of a diode which cathode is connected to a voltage source. A transducer (12) is connected at the drain of each MOSFET transistor and the voltage source. Each MOSFET transistor has protection diodes, which allows to protect the circuit against inductive loads and in general against countercurrents generated in the transducers.

Other power stages not illustrated are equally possible in different embodiment of the same invention.

Optionally, in a embodiment of the invention, the power stage of the transducer interface (7) comprises a relay circuit that allows the activation of the transducers of the transducer array.

Figure 6:
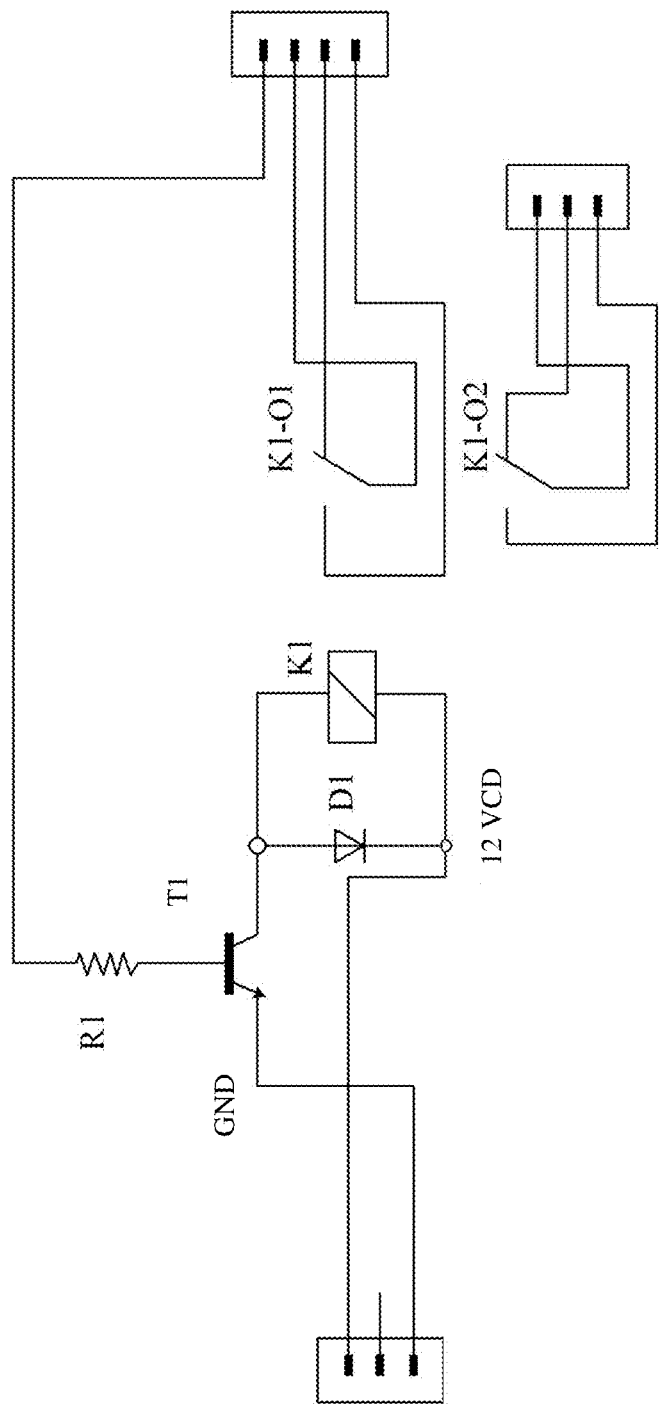
FIG. 6 shows an example of a relay circuit used to control the switching of the transducer array.

In FIG. 6, an example of a relay circuit is presented. The relay circuit consists of a pair of switches that allow selecting whether a transistor is conductive or not. When the transistor turns on, it allows the relay coil to connect to GND, changing the state of the relay.

The current invention is not limited to the models described and illustrated since as it may be evident to an skilled artisan, there are variations and possible modifications that do not depart from the spirit of the invention, which can only be defined by the following claims.

The invention claimed is:

1. A tissue stimulation device comprising:
   a power source;
   a control unit;
   a decoupled output stage circuit connected to the power source;
   a signal generator connected to an input of the decoupled output stage circuit and to the control unit;
   an analog demultiplexer connected to the decoupled output stage circuit by a first output signal and a second output signal, and the analog demultiplexer connected to the control unit, and
   a transducer array connected to an output of the analog demultiplexer;
   wherein the control unit selects the output of the analog demultiplexer that allows the switching of the first output signal and the second output signal to activate a plurality of transducers of the transducer array to stimulate a tissue,
   wherein the first output signal and the second output signal are configured to be any of an analog periodic signal, an analog non-periodic signal, a digital periodic signal, and a digital non-periodic signal.

2. The device of claim 1, wherein the analog demultiplexer is connected by a control bus to the control unit.

3. The device of claim 1, wherein the transducer array is connected by a data bus to the analog demultiplexer.

4. The device of claim 1, wherein the analog demultiplexer is connected by a data bus to a transducer interface having a power stage.

5. The device of claim 1, wherein the plurality of transducers is selected from the group consisting of Helmholtz coils, Peltier cells, heat generators, vibration motors, electrodes to induce an electric current, coils for inductive stimulation, antennas, and combinations thereof.

6. The device of claim 1, wherein the analog demultiplexer is connected by a data bus to a transducer interface having a power stage built with operational amplifiers.

7. The device of claim 1, wherein the analog demultiplexer is connected by a data bus to a transducer interface having a power stage built with transistors.

8. The device of claim 1, wherein the decoupled output stage circuit is also connected to the control unit.

9. A tissue stimulation device comprising:
   a power source;
   a plurality of transducers configured to stimulate tissue;
   an analog demultiplexer connected to the plurality of transducers;
   a decoupled output stage circuit having an input connected to the power source and an output connected to the analog demultiplexer;
   a control unit connected to an input of the analog demultiplexer for selectively activating the plurality of transducers through a signal; and
   a signal generator connected to an input of the decoupled output stage circuit and to an output of the control unit;
   wherein the decoupled output stage circuit has a first output signal and a second output signal, wherein the first output signal and the second output signal correspond to input signals of the analog demultiplexer,
   wherein the analog demultiplexer switches the first output signal and the second output signal according to the signal of the control unit.

10. The tissue stimulation device of claim 9, further comprising a transducer interface comprising transistors between the analog demultiplexer and the plurality of transducers.

11. The tissue stimulation device of claim 10, wherein the number of transistors corresponds to the number of transducers in the plurality of transducers.

12. The tissue stimulation device of claim 9, further comprising a transducer interface comprising an amplifier.

13. The tissue stimulation device of claim 9, wherein the decoupled output stage circuit is connected to the control unit.

14. The tissue stimulation device of claim 9, wherein the plurality of transducers comprises: Peltier cells, heat generators, vibration motors, electrodes, inductive coils, antennas, and combinations thereof.

15. A tissue stimulation device comprising:
a power source;
a plurality of transducers configured to stimulate tissue;
an analog demultiplexer configured to receive both an analog input and a digital input, said analog demultiplexer being connected to the plurality of transducers;
a decoupled output stage circuit having an output connected to the analog demultiplexer;
a control unit connected to an input of the analog demultiplexer for selectively activating the plurality of transducers and an input of a signal generator; and
the signal generator connected to an input of the decoupled output stage circuit,
wherein the control unit configures the analog demultiplexer to allow switching to activate the plurality of transducers to perform various forms of stimulation and prevent the plurality of transducers from overheating.

16. The tissue stimulation device of claim 15, further comprising a transducer interface comprising transistors between the analog demultiplexer and the plurality of transducers.

17. The tissue stimulation device of claim 15, further comprising a transducer interface comprising an amplifier.

18. The tissue stimulation device of claim 15, wherein the decoupled output stage circuit is connected to the control unit.

19. The tissue stimulation device of claim 15, wherein the plurality of transducers comprises: Peltier cells, heat generators, vibration motors, electrodes, inductive coils, antennas, and combinations thereof.

20. The tissue stimulation device of claim 15, wherein the decoupled output stage circuit is an isolation amplifier.

* * * * *